(12) United States Patent
Zhao et al.

(10) Patent No.: US 11,185,410 B2
(45) Date of Patent: Nov. 30, 2021

(54) BICUSPID VALVE PROSTHESIS, TRICUSPID VALVE PROSTHESIS, AND STENT THEREFOR

(71) Applicant: SHANGHAI MICROPORT CARDIOFLOW MEDTECH CO., LTD., Shanghai (CN)

(72) Inventors: Chunxia Zhao, Shanghai (CN); Ming Yang, Shanghai (CN); Guoming Chen, Shanghai (CN); Ming Liu, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 89 days.

(21) Appl. No.: 16/619,626

(22) PCT Filed: Jun. 7, 2018

(86) PCT No.: PCT/CN2018/090191
§ 371 (c)(1),
(2) Date: Dec. 5, 2019

(87) PCT Pub. No.: WO2018/223996
PCT Pub. Date: Dec. 13, 2018

(65) Prior Publication Data
US 2020/0138572 A1    May 7, 2020

(30) Foreign Application Priority Data

Jun. 9, 2017  (CN) .......................... 201710434531.5

(51) Int. Cl.
*A61F 2/24* (2006.01)
(52) U.S. Cl.
CPC .......... *A61F 2/2418* (2013.01); *A61F 2/2448* (2013.01); *A61F 2/2466* (2013.01)

(58) Field of Classification Search
CPC ........ A61F 2/2448; A61F 2/2466; A61F 2/24; A61F 2/2418
See application file for complete search history.

(56) References Cited

U.S. PATENT DOCUMENTS

| 5,817,126 A | 10/1998 | Imran |
| 2010/0049291 A1 | 2/2010 | Yampolsky et al. |

(Continued)

FOREIGN PATENT DOCUMENTS

| CN | 103228232 A | 7/2013 |
| CN | 105581858 A | 5/2016 |

(Continued)

*Primary Examiner* — Dinah Baria
(74) *Attorney, Agent, or Firm* — Muncy, Geissler, Olds & Lowe, P.C.

(57) ABSTRACT

A mitral valve prosthesis, a tricuspid valve prosthesis and a stent thereof. The stent is configured to support the heart valves of the mitral valve prosthesis and has a contracted configuration for delivery and an expanded configuration for deployment. The stent comprises, along its axial direction, an inflow section, a transition section and an outflow section, and the transition section is connected to the inflow section at one end and to the outflow section at the other end. When in the expanded configuration, the inflow section is located upstream of the outflow section with respect to the blood flow direction. The inflow section is less radially rigid than the outflow section and/or the transition section. Due to such a small radial rigidity, the inflow section can well adapt itself to the anatomy of the native mitral annulus. As a result, its pressure and interference on the aortic valve can be reduced, resulting in a significant decrease in the risk of leading to occlusion of the left ventricular outflow section. Additionally, during the release, the inflow section can adapt itself to changes in the diameter of the stent and thereby buffer radial deformation and axial displacement of the stent during its expansion, thus enhancing the release reliability.

17 Claims, 16 Drawing Sheets

(56) References Cited

U.S. PATENT DOCUMENTS

| | | | | |
|---|---|---|---|---|
| 2011/0270405 A1* | 11/2011 | Geitz | .................... | A61F 5/0076 |
| | | | | 623/23.7 |
| 2013/0172978 A1 | 7/2013 | Vidlund et al. | | |
| 2014/0142684 A1* | 5/2014 | Zukowski | ............... | A61F 2/852 |
| | | | | 623/1.16 |
| 2014/0214159 A1* | 7/2014 | Vidlund | .............. | A61L 27/3625 |
| | | | | 623/2.14 |
| 2016/0158000 A1* | 6/2016 | Granada | ............... | A61F 2/2418 |
| | | | | 623/2.18 |

FOREIGN PATENT DOCUMENTS

| | | |
|---|---|---|
| CN | 205612592 U | 10/2016 |
| CN | 106456325 A | 2/2017 |
| JP | 2016538949 A | 12/2016 |
| WO | WO0135864 A1 | 5/2001 |
| WO | WO-2013/028387 A2 | 2/2013 |
| WO | WO2013028387 A2 | 2/2013 |
| WO | WO-2015/179473 A1 | 11/2015 |
| WO | WO-2016/112085 A2 | 7/2016 |

\* cited by examiner

BICUSPID VALVE PROSTHESIS, TRICUSPID VALVE PROSTHESIS, AND STENT THEREFOR

TECHNICAL FIELD

The present invention relates to the technical field of medical prostheses and, more specifically, to a bicuspid valve prosthesis, a tricuspid valve prosthesis and a stent thereof.

BACKGROUND

A bicuspid valve, also known as a mitral valve, lies in the inflow section of the left ventricle and has a structure of a mitral valve complex including the mitral annulus, leaflets, chordae tendineae, papillary muscles, and even the ventricular wall, as suggested in some literatures. The mitral annulus is a dense connective tissue surrounding the left atrioventricular orifice, which has an anterior portion consisting of parts of the left and non-coronary annuli of the aortic valve sitting in the outflow section of the left ventricle and of the left and right fibrous trigones and a posterior portion providing attachment to the posterior leaflet. The anterior mitral leaflet is a fibrous extension of the aortic valve and forms, together with the posterior leaflet, the left ventricular inflow section. In addition, it defines the left ventricular outflow section together with the opposing heart septum. There is a risk of occlusion of the left ventricular outflow section resulting from an implanted prosthetic mitral valve.

The mitral chordae tendineae lie between the mitral valve leaflets and the myocardium and serve as a support connecting them. The subvalvular structure of the mitral valve plays an important role in maintaining the structure and functionality of the left heart. The subvalvular length and structure of any interventional prosthetic mitral valve must be so controlled and designed as to avoid exerting an adverse impact on the subvalvular structure of the native valve. On the other hand, since the mitral annulus is greater in diameter than the aortic valve, when a prosthetic mitral valve is delivered and released at the left atrioventricular orifice, it will experience a relatively large radial deformation, which, coupled with the relatively small subvalvular length of the prosthetic valve, will make a stent of the prosthesis difficult to be anchored and prone to significant axial displacement which may result in improper release and hence possible perivalvular leakage.

Patent publication WO2013028387 discloses an improved structure of prosthetic valve. The structure includes a stent and a valve assembly integrated with the stent. The stent is made of synthetic fabric material, cut tubular product or a combination of both. The most improvement provided by the patent publication lies in that the leaflet assembly is comprised of two layers of stabilized tissue respectively attached to the interior wall and the exterior wall of the stent. With such arrangement of the two layers of stabilized tissue, the stability of the prosthetic valve can be improved and the service life of the prosthetic valve can be prolonged. In the patent publication, the inflow section is formed by fabric material, thereby partially solving the problem of perivalvular leakage caused by axial displacement of the stent. However, since the causes of the perivalvular leakage are complex, it is desired to further improve the technical solution mentioned above.

SUMMARY OF THE DISCLOSURE

In view of the problem mentioned above, the present invention provides a mitral valve prosthesis, a tricuspid valve prosthesis and a stent thereof.

A stent, configured to support a mitral valve prosthesis or a tricuspid valve prosthesis, the stent having a contracted configuration for delivery and an expanded configuration for deployment, wherein the stent comprises, along an axial direction thereof, an inflow section, a transition section, an outflow section, the transition section having two ends respectively connected to the inflow section and to the outflow section; the inflow section is located, when in the expanded configuration, upstream of the outflow section with respect to a blood flow direction; the inflow section extends along the axial direction of the stent away from the transition section and flares out; the inflow section has a mesh structure formed by braided filaments; each of the transition section and the outflow section has a mesh structure formed by cutting a tube; the mesh structure of the inflow section is configured to cover an atrioventricular orifice and optionally further extends from an annulus over at least part of an atrium when the stent has been deployed and is in the expanded configuration.

In one embodiment, the mesh structure of the inflow section comprises a plurality of first mesh cells;
the plurality of first mesh cells are arranged in one row and of a same size, or
the plurality of first mesh cells are arranged in a plurality of rows each of which contains equally sized ones of the plurality of first mesh cells, and sizes of the plurality of first mesh cells arranged in the plurality of rows increase row by row from one of the rows proximal to the transition section to one of the rows distal from the transition section.

In one embodiment, the mesh structure of the inflow section comprises a plurality of first mesh cells at least some of which are different in axial length from others.

In one embodiment, the plurality of first mesh cells are arranged in one row, and wherein in the expanded configuration, those out of the first mesh cells corresponding to an anterior portion of a native annulus are axially longer than those of the first mesh cells corresponding to a posterior portion of the native annulus.

In one embodiment, in the expanded configuration, the inflow section has a width ranging from 30 mm to 65 mm at an end distal from the transition section.

In one embodiment, in the expanded configuration, the transition section has a minimum width ranging from 25 mm to 50 mm in order to fit a native annulus.

In one embodiment, at least part of the filaments forming the mesh structure of the inflow section are connected to the transition section by braiding.

In one embodiment, the transition section comprises a plurality of second mesh cells which are arranged in one or more rows;
at least some of the second mesh cells at an end of the transition section proximal to the inflow section are provided with connecting holes, and the filaments of the inflow section pass through at least some of the connecting holes before forming those of the first mesh cells adjacent to the transition section, or the filaments of the inflow section wound around at least some of the second mesh cells at an end of the transition section proximal to the inflow section before forming those of the first mesh cells adjacent to the transition section, or
at least some of the second mesh cells at an end of the transition section proximal to the inflow section are provided with connecting rods projecting away from the inflow section, and the filaments of the inflow section are wounded over the connecting rods or around those of the second mesh cells near the connecting rods.

In one embodiment, the transition section comprises a plurality of second mesh cells which are arranged in one or more rows;

connecting holes are provided near apices of at least some of the second mesh cells located at an end of the transition section proximal to the inflow section, and the filaments of the inflow section pass through at least some of the connecting holes before forming those of the first mesh cells adjacent to the transition section, or the filaments of the inflow section wound for at least one turn around apices of at least some of the second mesh cells located at an end of the transition section proximal to the inflow section before forming those of the first mesh cells adjacent to the transition section, or connecting rods projecting away from the inflow section are provided near apices of at least some of the second mesh cells located at an end of the transition section proximal to the inflow section, and the filaments of the inflow section are wounded over the connecting rods or around those of the second mesh cells near the connecting rods.

In one embodiment, at least part of the filaments forming the mesh structure of the inflow section are connected to the transition section by welding, riveting or screwing.

In one embodiment, the mesh structure of the inflow section comprises a plurality of first mesh cells, and the mesh structure of the transition section comprises a plurality of second mesh cells, and wherein at least one annular connecting member is formed around an apex of each of at least some of the first mesh cells of the inflow section proximal to the transition section, at least one connecting hole is provided on at least some of the second mesh cells of the transition section proximal to the inflow section, and the transition section and the inflow section are fixedly connected by inserting a rivet through each of the at least one annular connecting member and a corresponding one of the at least one connecting hole.

In one embodiment, the mesh structure of the inflow section comprises a plurality of first mesh cells, and the mesh structure of the transition section comprises a plurality of second mesh cells, and wherein at least one annular connecting member is formed around an apex of each of at least some of the first mesh cells of the inflow section proximal to the transition section, at least one threaded hole is provided on at least some of the second mesh cells of the transition section proximal to the inflow section, and the transition section and the inflow section are fixedly connected by inserting a screw through each of the at least one annular connecting member and a corresponding one of the at least one threaded hole to form a threaded connection between the screw and a corresponding one of the second mesh cells.

In one embodiment, at least part of the filaments forming the mesh structure of the inflow section are indirectly connected to the transition section.

In one embodiment, further comprising a connecting feature having one end secured to the inflow section and another end secured to the transition section and/or the outflow section.

In one embodiment, the mesh structure of the inflow section comprises a plurality of first mesh cells, and the mesh structure of the transition section comprises a plurality of second mesh cells, and wherein at least one annular connecting member is formed around an apex of each of at least some of the first mesh cells of the inflow section proximal to the transition section, at least one connecting hole is provided on at least some of the second mesh cells of the transition section proximal to the inflow section, and the stent comprises at least two connecting features each having two ends respectively connected to one of the annular connecting features and to one of the connecting holes.

In one embodiment, the mesh structure of the inflow section comprises a plurality of first mesh cells, and the mesh structure of the transition section comprises a plurality of second mesh cells, and wherein the connecting feature is a sheet-like member which is made of a macromolecular material and has two ends one secured to the inflow section and the other to the transition section and/or the outflow section.

In one embodiment, the mesh structure of the outflow section comprises a plurality of third mesh cells which are arranged in one or more rows and are arranged in connection with or separated from each other.

In one embodiment, the mesh structures of the outflow section and the transition section are integrally fabricated by cutting a single tube.

In one embodiment, in the expanded configuration, a total axial length of the transition section and the outflow section ranges from 1 cm to 3.5 cm.

In one embodiment, an end of the outflow section distal from the transition section is not lower than a free edge of at least one of native valve leaflets when the stent has been deployed and is in the expanded configuration.

In one embodiment, when the stent has been deployed and is in the expanded configuration, the end of the outflow section distal from the transition section is situated between a free edge of an anterior leaflet and an anterior portion of the annulus, and is axially close to a free edge of a posterior leaflet.

In one embodiment, further comprising anchoring means disposed over the transition section and/or over the outflow section.

A mitral valve prosthesis, comprising
a valve assembly; and
the stent as mentioned above, to which the valve assembly is attached.

In one embodiment, the valve assembly comprises a prosthetic leaflet and a skirt in connection with the prosthetic leaflet; the prosthetic leaflet is secured to both of the transition section and the outflow section; the skirt is secured to both of the inflow section and the transition section, or to each of the inflow section, the transition section and the outflow section.

A tricuspid valve prosthesis, comprising
a valve assembly; and
the stent as mentioned above, to which the valve assembly is attached.

In one embodiment, the valve assembly comprises a prosthetic leaflet and a skirt in connection with the prosthetic leaflet; the prosthetic leaflet is secured to both of the transition section and the outflow section; the skirt is secured to both of the inflow section and the transition section, or to each of the inflow section, the transition section and the outflow section.

In the mitral valve prosthesis, the tricuspid valve prosthesis and the stent thereof, as defined above, as the inflow section is formed by braided filaments, it has a small radial rigidity and its shape can well conform to the anatomy of the native mitral annulus. As a result, the pressure and interference on the aortic valve can be reduced, resulting in a significant decrease in the risk of leading to occlusion of the left ventricular outflow section. Moreover, during the release, the inflow section can adapt itself to changes in the diameter of the stent and thereby buffer radial deformation and axial displacement of the stent during its expansion, thus enhancing the release reliability. In addition, as the inflow section is less rigid than the outflow section and/or the transition section, the part of a delivery system in which the inflow section is loaded is easily bendable to a certain angle, which facilitates the conformance to the anatomy of blood vessels and the advancement of the delivery system in the human body.

BRIEF DESCRIPTION OF THE DRAWINGS

In order to more clearly explain embodiments of the present invention or the conventional solutions, a brief description of the drawings used in the explanation will be set forth below. It is apparent that these drawings present only some embodiments of the present invention and those skilled in the art may obtain drawings of other embodiments from them without exerting any creative effort.

DETAILED DESCRIPTION

In order to facilitate the understanding of the present invention, the invention is now described more fully hereinafter with reference to the accompanying drawings, in which preferred embodiments thereof are shown. This invention may, however, be embodied in many different forms and should not be construed as limited to the embodiments set forth herein. Rather, these embodiments are provided so that this disclosure will be thorough and complete.

Unless otherwise defined, all technical and scientific terms used herein have the same meaning as commonly understood by those of ordinary skill in the art. The terminology used herein is for the purpose of describing particular embodiments only and is not intended to be limiting of the invention. As used herein, the term "and/or" includes any and all combinations of one or more of the associated listed items.

Figure 1:
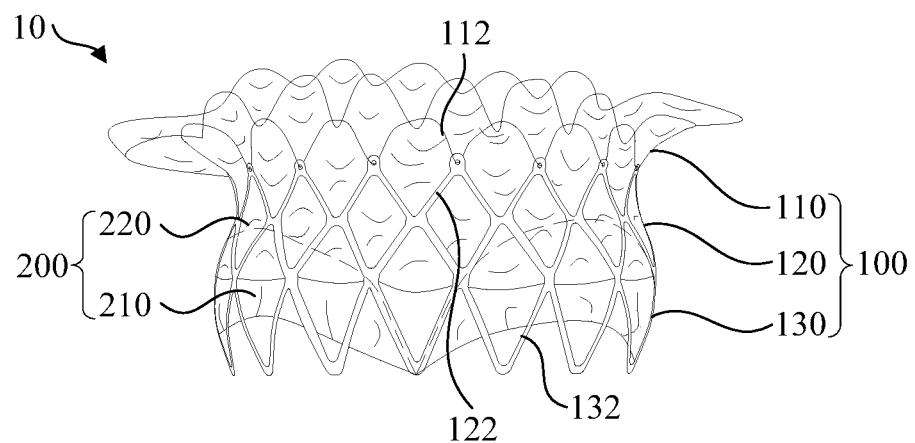
FIG. 1 is a perspective view of a mitral valve prosthesis according to an embodiment.

As shown in FIG. 1, a mitral valve prosthesis 10 according to an embodiment is configured to replace a native mitral valve. The mitral valve prosthesis 10 includes a stent 100 and a valve assembly 200 that is attached to the stent 100. The stent 100 is configured to support the valve assembly 200 and may have a contracted configuration for delivery and an expanded configuration for deployment. The stent 100 includes, along its axial length, an inflow section 110, an outflow section 130 and a transition section 120 having two ends respectively connected to the inflow section 110 and to the outflow section 130. In the expanded configuration, the inflow section 110 is located upstream of the outflow section 130 with respect to the blood flow direction. The inflow section 110 is less radially rigid than the outflow section 130 and/or the transition section 120.

In the expanded configuration, the inflow section 110 extends away from the transition section 120 along the axial direction of the stent 100 and flares out. The inflow section 110 may generally assume a flared shape or consist of a tubular portion in connection with the transition section 120 and a flared portion distal from the transition section 120. The flare can fit closely to the inner wall of the atrium, making the mitral valve prosthesis 10 possible to be more firmly anchored in the heart.

The inflow section 110 is a mesh structure braided from filaments, and the transition section 120 and the outflow section 130 are mesh structures fabricated by cutting tubes. Obviously, the mesh structure braided from filaments is less radially rigid than the mesh structures fabricated from cutting tubes. Due to such a low radial rigidity, the inflow section 110 can better adapt in shape to the native mitral annulus, with lower pressure and interference on the aortic valve and a significantly reduced risk of leading to occlusion of the left ventricular outflow section. In addition, the inflow section 110 easily adapts itself to changes in the diameter of the stent 100 occurring during the release of the implant and thereby buffer radial deformation and axial displacement of the expanding stent 100. As a result, more reliable release can be achieved. Further, since the inflow section 110 is less rigid than the outflow section 130 and/or the transition section 120, the portion of a delivery system in which the inflow section 110 is loaded can be bent to a certain angle to conform to the anatomy of blood vessels in the body, which facilitates the advancement of the delivery system in the body.

The inflow section 110 has a plurality of first mesh cells 112. In particular, the plurality of first mesh cells 112 may be formed by one or more zigzag filaments that are arranged in a certain way, or connected together optionally by welding, riveting or braiding. These filaments are made of a biocompatible shape memory material such as a nickel-titanium (NiTi) alloy.

In one embodiment, the inflow section 110 has a D-shaped or elliptical cross section at a position proximal to the transition section 120. In other words, in the expanded configuration, when viewed at the end where the blood flows in, the inflow section 110 is D-shaped or elliptical at the narrowest part. This shape is compatible with the shape of the atrioventricular orifice, and when the inflow section 110 is D-shaped, the straight vertical edge is close to the anterior portion of the mitral annulus.

Figure 2:
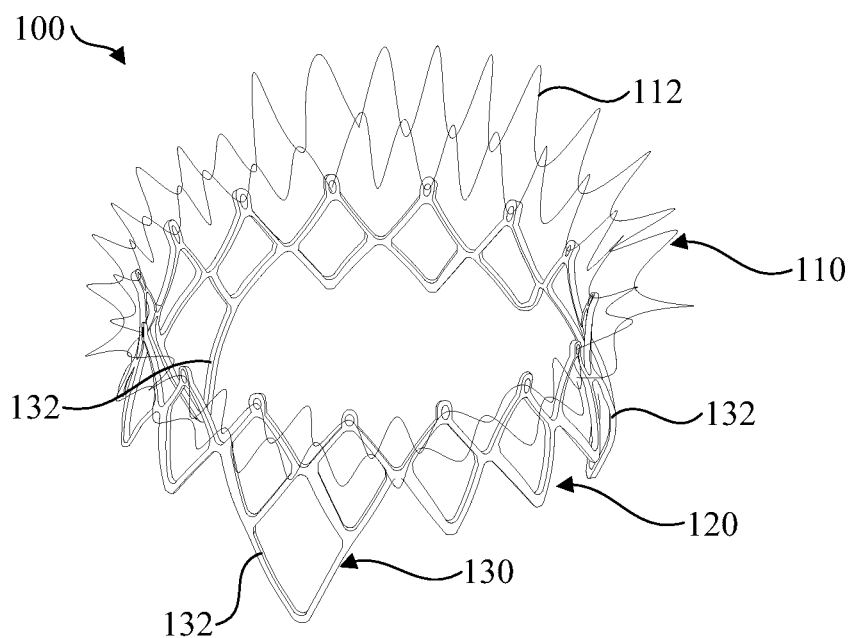
FIG. 2 is a perspective view of a stent for a mitral valve prosthesis according to a further embodiment.

In one embodiment, the mesh structure of the inflow section 110 includes a plurality of first mesh cells 112. In one embodiment, the plurality of first mesh cells 112 are arranged in one row and may be of the same size. In another embodiment, the plurality of first mesh cells 112 are arranged in several rows each containing equally sized first mesh cells 112, and the size of first mesh cells 112 increases row by row from the end adjacent to the transition section 120 to the end distal from the transition section 120. In a further embodiment, at least some of the first mesh cells 112 may have different axial dimensions. For example, in one or more of the rows, there may be some first mesh cells 112 with different axial dimensions, which correspond to a certain site. Referring to FIG. 2, in one embodiment, the plurality of first mesh cells 112 are arranged in one row and, in the expanded configuration, those of the first mesh cells 112 corresponding to the anterior portion of the native mitral annulus are axially longer than those corresponding to the posterior portion of the native mitral annulus. With such a design, after the mitral valve prosthesis 10 is released, the portion of an outer edge of the inflow section 110 facing anterior mitral annulus is higher than the portion facing posterior mitral annulus. The left atrium above the anterior portion of the mitral annulus has a large area, which can disperse the pressure of the prosthesis on the left atrium and hence reduce the pressure on the aortic valve, resulting in a lowered risk of occlusion of the left ventricular outflow section.

In one embodiment, in the expanded configuration, the inflow section 110 has a width ranging from 30 mm to 65 mm at the end distal from the transition section 120. The width of the inflow section 110 is necessarily greater than the diameter of the native mitral annulus, in order to prevent the mitral valve prosthesis 10 from dislodgement into the ventricle during diastole. In one embodiment, the mitral valve prosthesis 10 may be sized depending on the size of the patient's heart.

Figure 3:
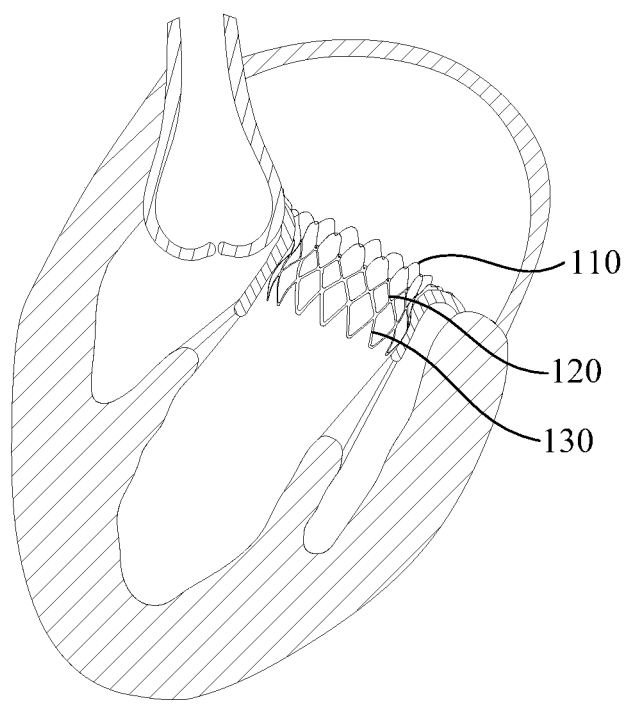
FIG. 3 is a schematic diagram illustrating a mitral valve prosthesis in use according to a further embodiment.

Referring to FIG. 3, in one embodiment, the inflow section 110 may cover the left atrioventricular orifice, with its end distal from the transition section 120 neither in contact with the aortic-mitral curtain nor with the aortic valve when in the expanded configuration.

Figure 4:
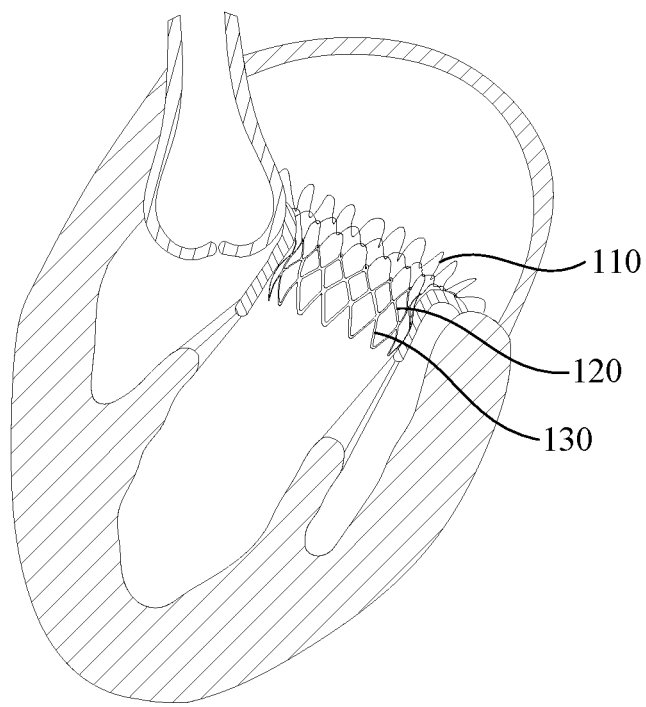
FIG. 4 is a schematic diagram illustrating of a mitral valve prosthesis in use according to a further embodiment.
Figure 5:
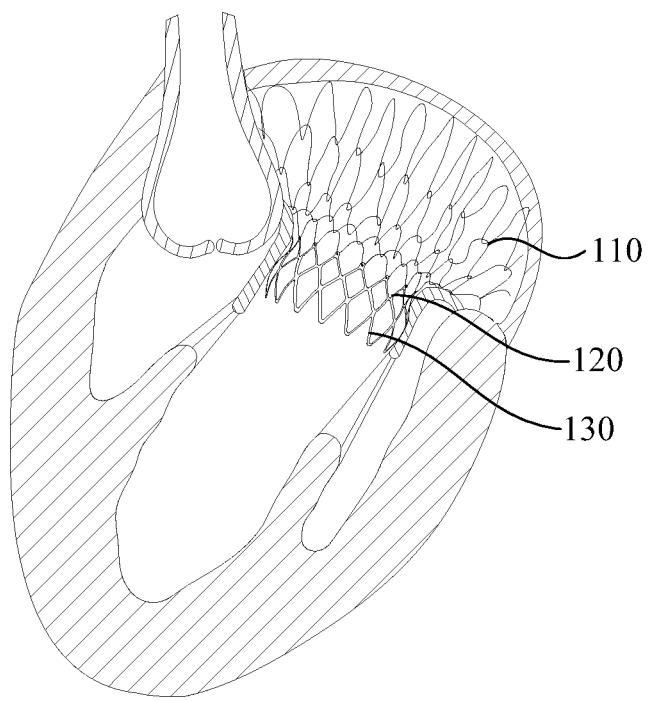
FIG. 5 is a schematic diagram illustrating of a mitral valve prosthesis in use according to a further embodiment.

Referring to FIG. 4, in an alternative embodiment, the inflow section 110 may cover the atrioventricular orifice, extend from the mitral annulus over the aortic-mitral curtain toward the left atrium, and end at a distal end of the curtain. As the inflow section 110 is braided from filaments, it is soft and flexible. When delivered over the native aortic valve, it can conform to the anatomy thereof without exerting a significant pressure thereon. Further, referring to FIG. 5, the inflow section 110 may further alternatively cover the atrioventricular orifice and extend from the mitral annulus toward the left atrium and extend over the entire left atrium.

Referring again to FIG. 1, two ends of the transition section 120 may be directly or indirectly connected to the blood outflow end of the inflow section 110 and to the blood inflow end of the outflow section 130, respectively. The transition section 120 includes a mesh structure formed of a plurality of second mesh cells 122 and is fabricated by cutting a tube made of a biocompatible shape memory material using, for example, a cold laser.

In one embodiment, in the expanded configuration, in order to fit the native mitral annulus without perivalvular leakage, the transition section 120 may have a minimum width ranging from 25 mm to 50 mm. In general, the transition section 120 may have a minimum diameter that is not less than the diameter of the native mitral annulus.

Figure 6A:
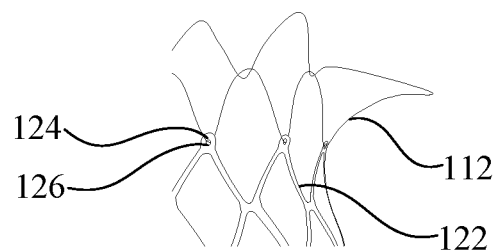
FIG. 6a is a schematic diagram illustrating a connection between an inflow section and a transition section in a mitral valve prosthesis according to a further embodiment.

In one embodiment, at least part of the filaments from which the mesh structure of the inflow section 110 is fabricated are connected to the transition section 120 by braiding. Referring to FIG. 6a, in one embodiment, connecting holes 126 are defined around apices 124 of respective second mesh cells 122 at the end of the transition section 120 proximal to the inflow section 110, through which filaments of the inflow section 110 pass and form first mesh cells 112 adjacent to the transition section 120. Specifically, during the fabrication, the filaments by braiding which the inflow section 110 is formed may be zigzag and pass through the connecting holes 126 and then form the first mesh cells 112 of the inflow section 110. As will be appreciated by those skilled in the art, while the connecting holes 126 have been described above as being positioned around the apices 124, the present invention is not so limited because they may also be defined at any positions on the respective second mesh cells 122 at the end of the transition section 120 proximal to the inflow section 110. All or only some of the second mesh cells 122 at the end proximal to the inflow section 110 may each define a connecting hole 126 around its apex 124. The filaments of the inflow section 110 may pass through all or only some of the connecting holes 126.

Figure 6B:
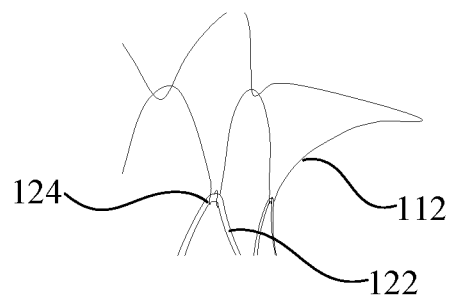
FIG. 6b is a schematic diagram illustrating a connection between an inflow section and a transition section in a mitral valve prosthesis according to a further embodiment.

In one embodiment, the connecting holes 126 may be omitted, and the filaments of the inflow section 110 may be directly secured to the second mesh cells 122 of the transition section 120. Referring to FIG. 6b, in one embodiment, the filaments of the inflow section 110 may be wound for at least one turn around the apices 124 of the respective second mesh cells 122 at the end of the transition section 120 proximal to the inflow section 110 and then form the first mesh cells 112 adjacent to the transition section 120. The filaments of the inflow section 110 may be wound for one or more turns. As will be appreciated by those skilled in the art, while the filaments of the inflow section 110 have been described above as being connected around the apices 124 of the second mesh cells 122 at the end proximal to the inflow section 110, the present invention is not so limited because they may also be connected at other places around the second mesh cells 122, for example, around their other corners, more particularly, the corners shared with adjacent second mesh cells 122. The filaments of the inflow section 110 may be wound around the apices 124 of all or only some of the second mesh cells 122 at the end proximal to the inflow section 110.

Figure 6C:
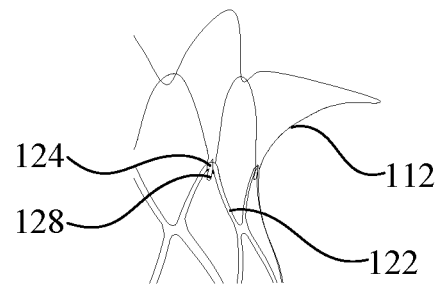
FIG. 6c is a schematic diagram illustrating a connection between an inflow section and a transition section in a mitral valve prosthesis according to a further embodiment.

In order to prevent dislocation of the filaments connected around the apices 124 of the second mesh cells 122, in one embodiment, anchoring features such as connecting rods 128 may be provided around the apices 124 of the second mesh cells 122. Referring to FIG. 6c, around the apex 124 of each of the second mesh cells 122 at the end of the transition section 120 proximal to the inflow section 110, there may be provided one connecting rod 128, or more connecting rods 128 in an alternative embodiments. The connecting rods 128 may extend away from the inflow section 110, and the filaments of the inflow section 110 may be wound over the connecting rods 128 or around some of the second mesh cells 122 near the connecting rods 128. As will be appreciated by those skilled in the art, while the anchoring features have been described above as being provided around the apices 124, the present invention is not so limited, because they may also be provided anywhere else on the second mesh cells 122 at the end of the transition section 120 proximal to the inflow section 110. The connecting rods 128 may be provided around all or only some of the second mesh cells 122 at the end of the transition section 120 proximal to the inflow section 110.

Figure 7A:
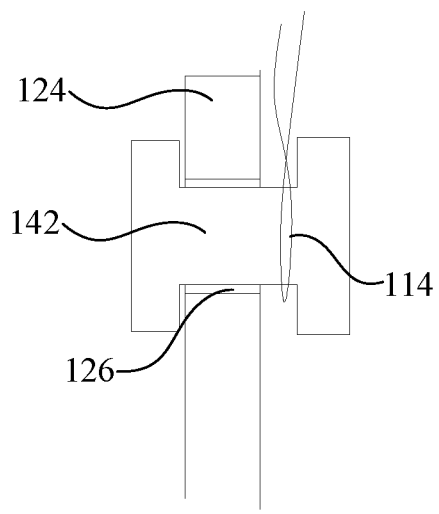
FIG. 7a is a schematic diagram illustrating a connection between an inflow section and a transition section in a mitral valve prosthesis according to a further embodiment.
Figure 7B:
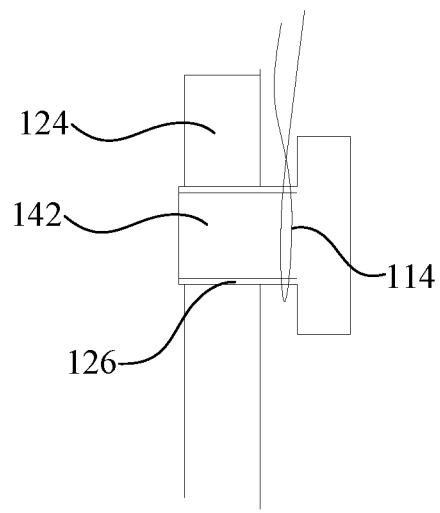
FIG. 7b is a schematic diagram illustrating a connection between an inflow section and a transition section in a mitral valve prosthesis according to a further embodiment.

In other embodiments, the inflow section 110 may be connected to the transition section 120 by welding, riveting, screwing or the like. Referring to FIG. 7a, in one embodiment, the inflow section 110 may be defined with at least one annular connecting member 114 around the apex of each of their first mesh cells 112 proximal to the transition section 120, and connecting holes 126 are defined around at least some of the second mesh cells 122 of the transition section 120 proximal to the inflow section 110. In one embodiment, the connecting holes 126 may be located around the apices 124 of the second mesh cells 122. Rivets 142 pass through the annular connecting members 114 and are securely connected to corresponding ones of the connecting holes 126 so that the transition section 120 is fixedly attached to the inflow section 110. Referring to FIG. 7b, in one embodiment, connecting holes 126 with internal threads, i.e., threaded holes, are defined around at least some of the second mesh cells 12 of the transition section 120 proximal to the inflow section 110. In one embodiment, the threaded holes may be defined around the apices of the second mesh cells 122. Screws 144 are inserted through the annular connecting members 114 and screwed into corresponding ones of the threaded holes of the second mesh cells 122, thereby fixedly connecting the transition section 120 to the inflow section 110. Similarly, the connecting holes 126 are not limited to the positions around the apices 124.

Figure 8A:
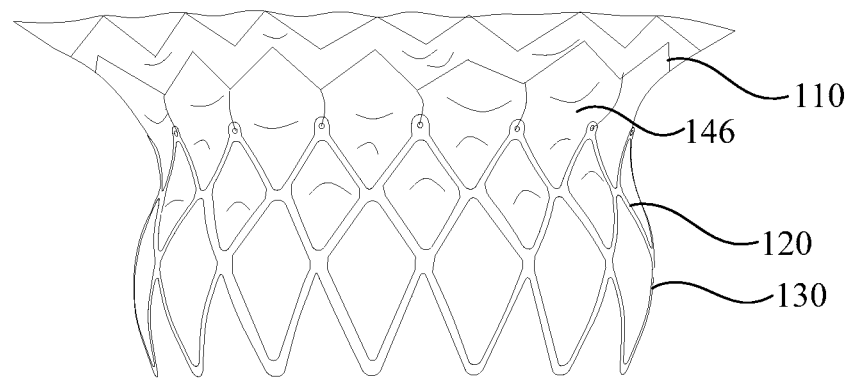
FIG. 8a is a schematic diagram illustrating a connection between an inflow section and a transition section in a mitral valve prosthesis according to a further embodiment.
Figure 8B:
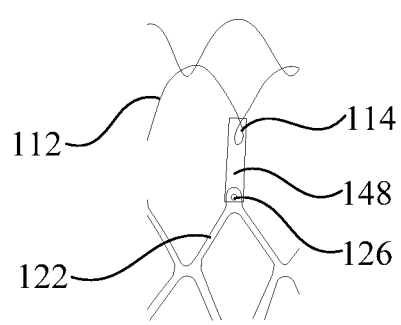
FIG. 8b is a schematic diagram illustrating a connection between an inflow section and a transition section in a mitral valve prosthesis according to a further embodiment.

Alternatively, the inflow section 110 may be indirectly connected to the transition section 120 via connecting features. Referring to FIG. 8a, in one embodiment, the connecting feature 146 may be a sheet-like member, which for example is a skirt, made of a biocompatible macromolecular material. The connecting feature 146 may have one end secured to the inflow section 110 and the other end attached to the transition section 120 and/or the outflow section 130 either by sewing or bonding. Referring to FIG. 8b, in one embodiment, the inflow section 110 may be provided with at least one annular connecting member 114 around the apex of each of their first mesh cells 112 proximal to the transition section 120, and connecting holes 126 are defined around at least some of the second mesh cells 122 of the transition section 120 proximal to the inflow section 110. In one embodiment, the connecting holes 126 may be located around the apices 124 of the second mesh cells 122. Similarly, the connecting holes 126 are not limited to the positions around the apices 124. The stent may have at least two connecting features 148 each in connection, at one end, with one of the annular connecting members 114 and, at the other end, with a corresponding one of the connecting holes 126.

Referring again to FIG. 1, in one embodiment, the valve assembly 200 includes a prosthetic leaflet 210 and a skirt 220 in connection with the prosthetic leaflet 210. The prosthetic leaflet 210 is attached to both the transition section 120 and the outflow section 130. The skirt 220 may either be attached to the inflow section 110 and the transition section 120, or to the inflow section 110, the transition section 120 and the outflow section 130. The attachment may be accomplished by sewing or bonding. The prosthetic leaflet 210 in the valve assembly 200 may be derived from a homogeneous or heterogeneous biological material such as porcine or bovine pericardium. The skirt 220 may be formed of a biocompatible material such as a processed animal pericardium or a biocompatible macromolecular material such as, for example, polyethylene terephthalate (PET), polyethylene (PE), polytetrafluoroethylene (PTFE) or the like.

The outflow section 130 is connected to the blood outflow end of the transition section 120, and may be spherically, ovally, cylindrically or conically curved. The mesh structure of the outflow section 130 includes a plurality of third mesh cells 132 and may be fabricated by cutting a tube made of a biocompatible shape memory material. In one embodiment, the outflow section 130 is formed by cutting the tube using a cold laser. In one embodiment, the mesh structures of the outflow section 130 and the transition section 120 may be integral and fabricated by cutting a single tube. This can make the fabrication easier and result in a firm connection between them.

Figure 9:
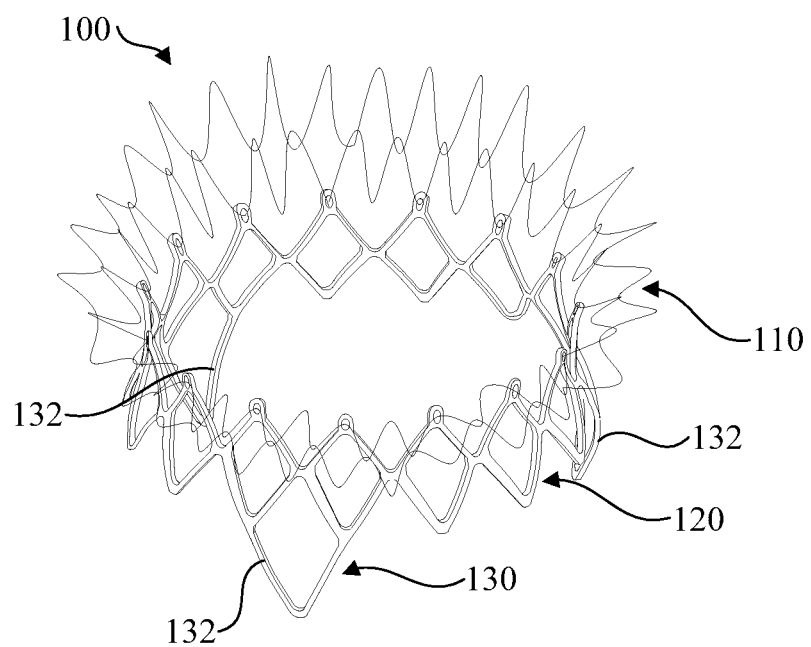
FIG. 9 is a perspective view of a stent of a mitral valve prosthesis according to a further embodiment.

In one embodiment, the plurality of third mesh cells 132 may be arranged in one or more rows and may be connected with, or separated from, each other. Referring again to FIG. 1, in one embodiment, the plurality of third mesh cells 132 may be arranged in one row where they are uniformly distributed circumferentially in connection with each other. Referring to FIG. 9, in one embodiment, the plurality of third mesh cells 132 may be arranged in one row where they are circumferentially distributed and separated from each other.

In one embodiment, the transition section 120 and the outflow section 130 may serve as subvalvular members of the mitral valve prosthesis 10, and in the expanded configuration, a total axial length of the transition section 120 and the outflow section 130 may range from 1 cm to 3.5 cm. In one embodiment, the end of the outflow section 130 distal from the transition section 120 may be positioned not lower than a free edge of at least one of the native mitral valve leaflets. Referring again to FIG. 3, the end of the outflow section 130 distal from the transition section 120 may be located between a free edge of the anterior mitral leaflet and the anterior portion of the mitral annulus and axially close to a free edge of the posterior mitral leaflet. Since the mitral valve chordae tendineae, which project from the myocardial wall and the papillary muscles to the free edges of the leaflets, anchors the leaflets and hence plays an important role in maintaining the shape of the left ventricle, rupture of the chordae tendineae may cause reshaping of the left ventricle, or free movement of the leaflets due to a lack of constraints, which may induce hemodynamic abnormalities. The subvalvular members of the mitral valve prosthesis 10 should not be too long in order to avoid adversely affecting the functionality of the chordae tendineae. The mitral valve prosthesis 10 according to the foregoing embodiments can significantly reduce the risk of leading to occlusion of the left ventricle outflow section.

The transition section 120 and the outflow section 130 are the portions of the stent 100 where the prosthetic leaflet 210 is attached, and may be structured and sized as required by prosthetic leaflet 210. That is, the transition section 120 may have an inner diameter that is less than or equal to a diameter of the prosthetic leaflet 210 when it closes with its free edges coming into contact with each other, and the total length of the transition section 120 and the outflow section 130 may be greater than or equal to a sewn length of the prosthetic leaflet 210.

The transition section 120 and the outflow section 130 are both more radially rigid than the inflow section 110. During contraction of the ventricle, the prosthetic leaflet 210 closes, and the radially rigid transition section 120 and outflow section 130 can withstand the pulling force from the prosthetic leaflet 210 without significant deformation, thereby reducing the risk of perivalvular leakage arising from insufficient closure of the prosthetic leaflet 210 due to deformation of the stent 100.

As a one-way valve for blood flow from the left atrium to the left ventricle, the mitral valve includes the mitral annulus continuous with the aortic annulus extension and with the myocardial wall, the two asymmetrical mitral leaflets, the chordae tendineae that anchor the leaflets and the papillary muscles attached to the myocardial wall. Due to such a complex structure of the mitral valve, the mitral valve prostheses 10 for transcatheter implantation may be generally provided with additional anchoring means disposed over the transition section 120 and/or the outflow section 130 for securing the attachment of the mitral valve prosthesis 10 to the native mitral valve. According to the present invention, the anchoring means is not limited to any particular shape or position and can use any existing or future technique in the art. For example, one or more anchors may be provided at the junction between the transition section 120 and the outflow section 130. Alternatively, one or more anchors may be provided between the third mesh cells 132 of the outflow section 130.

In one embodiment, the mitral valve prosthesis 10 according to the foregoing embodiments may be loaded in a manner as described below.

Figure 10A:
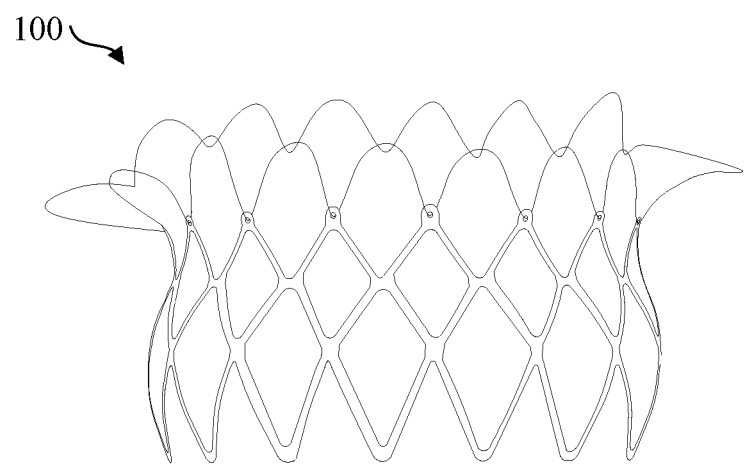
FIGS. 10a, 10b, 11a, 11b, 11c, 11d, 12a, 12b, 13, 14a, 14b, 14c and 15 are schematic diagrams illustrating a process of loading the mitral valve prosthesis of FIG. 1.
Figure 10B:
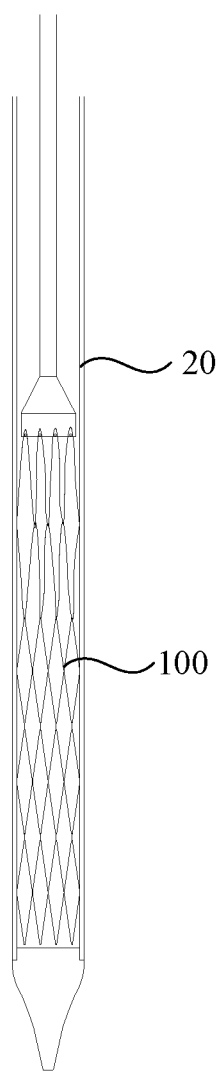
Figure 11A:
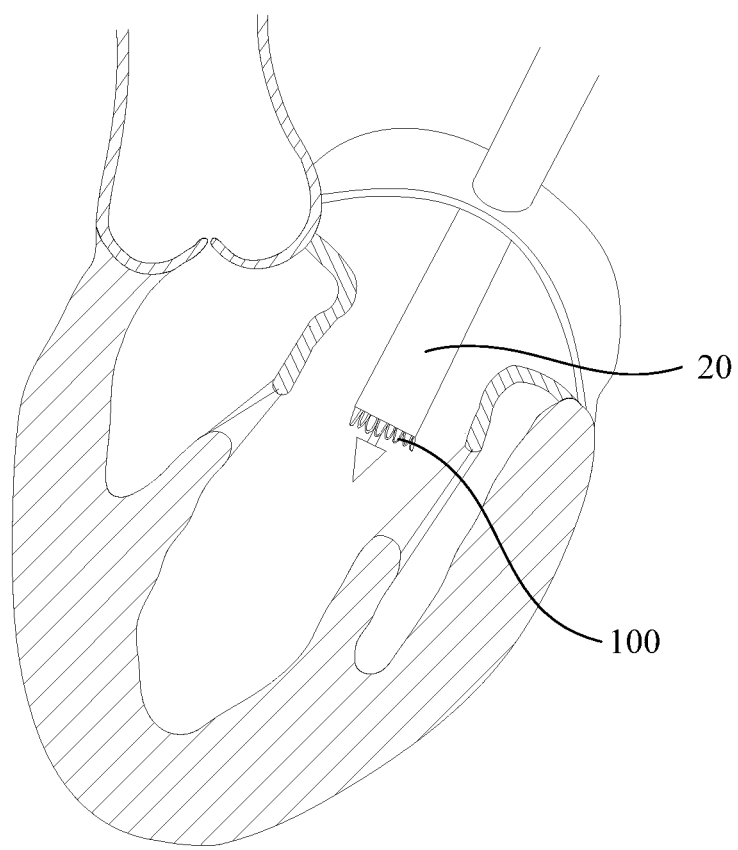
Figure 11B:
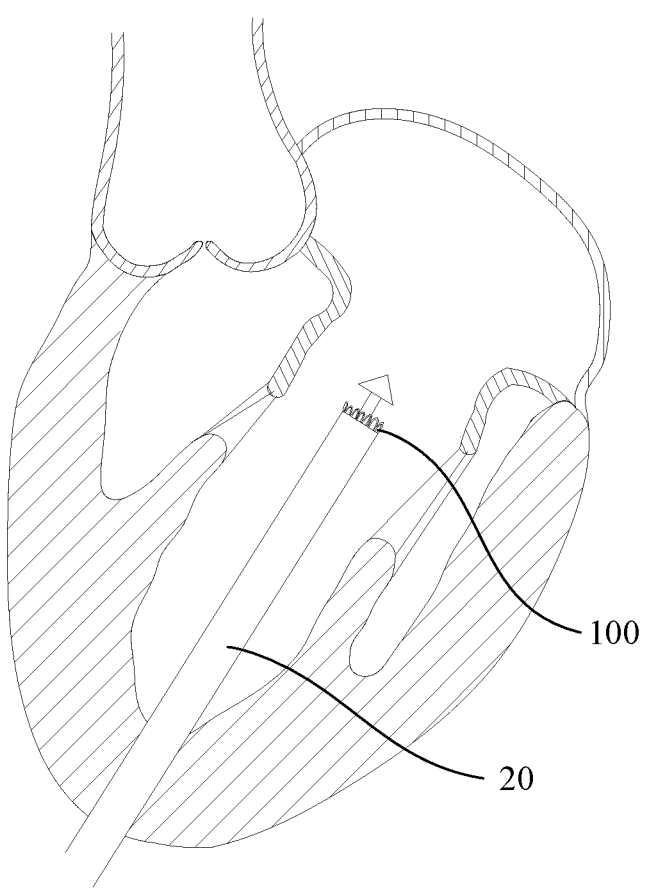
Figure 11C:
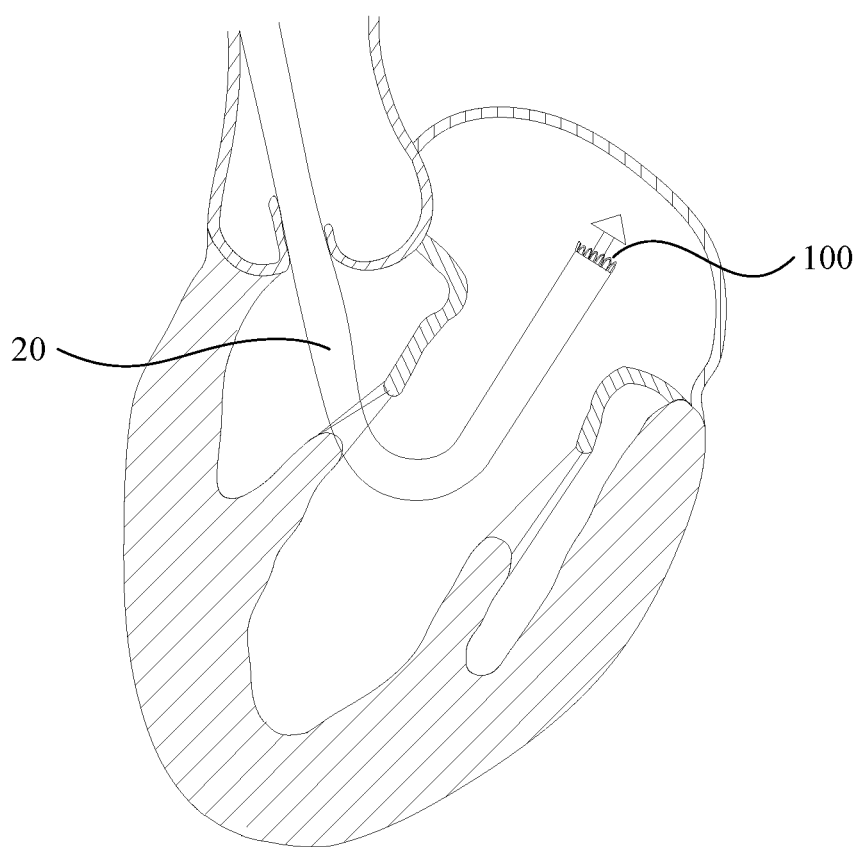
Figure 11D:
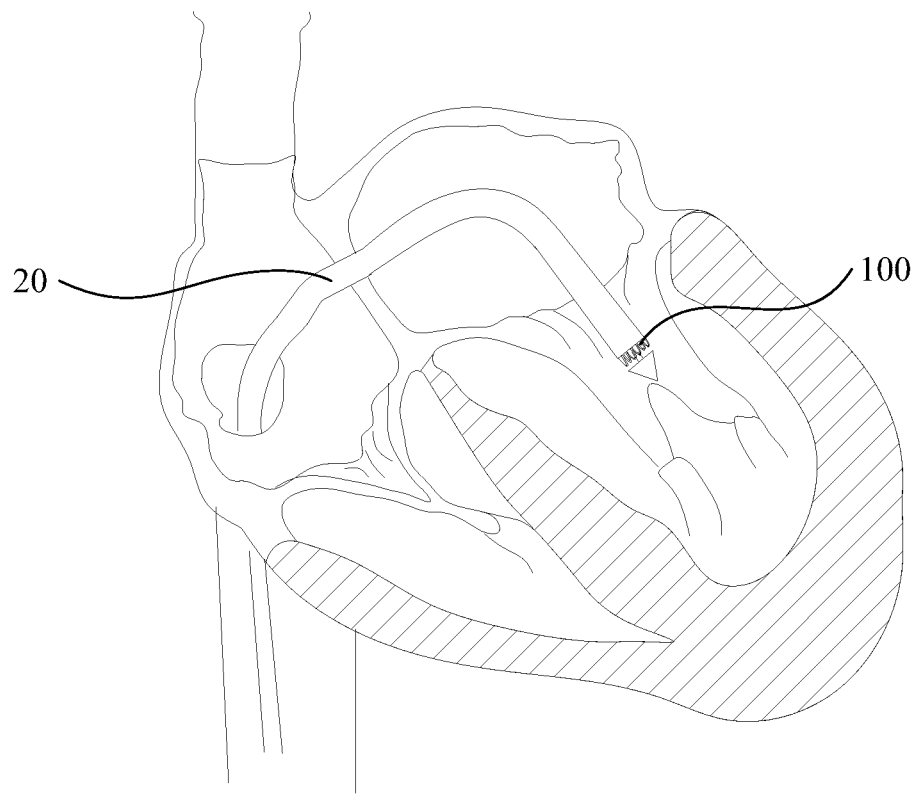

Referring to FIGS. 10a and 10b, before the mitral valve prosthesis 10 is loaded into the delivery system 20, the stent 100 assumes the expanded configuration with a great circumferential diameter and a small axial length. When the mitral valve prosthesis 10 is loaded in the delivery system 20, the stent 100 assumes the contracted configuration with a reduced circumferential diameter and an increased axial length. The mitral valve prosthesis 10 may be loaded into the delivery system 20 with the aid of an external tool so that the stent 100 shifts from the expanded configuration to the contracted configuration in a particular circumstance. For example, the mitral valve prosthesis 10 may be contracted to a circumferential dimension that allows it to be loaded into the delivery system 20 by means of passing through a tool with a circumferentially tapered conical surface.

Depending on the delivery route of the delivery system 20, the position at which the stent 100 is connected to the delivery system 20 may be adjusted according to specific conditions. In one embodiment, referring to FIGS. 11a to 11d, the stent 100 may be so connected to the delivery system 20 as to be suitable for trans-left atrial, transapical, transseptal or transaortic delivery. In the case of trans-left atrial or transseptal delivery, the stent 100 may be connected to the delivery system 20 at the end of the inflow section 110 distal from the transition section 120, while in the case of transapical or transaortic delivery, the stent 100 may be connected to the delivery system 20 at the end of the outflow section 130 distal from the transition section 120.

Figure 12A:
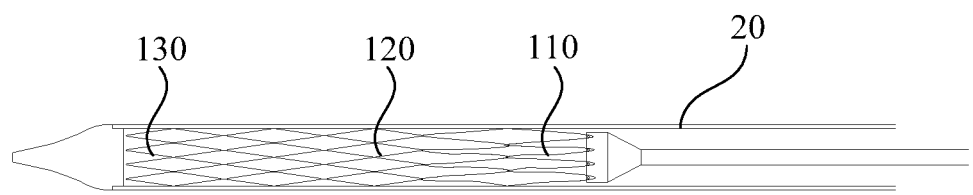
Figure 12B:
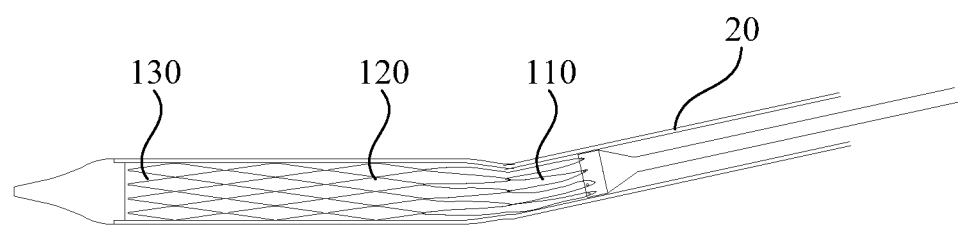

As shown in FIGS. 12a and 12b, as the inflow section 110 is a braided member, it is still relatively low in rigidity after the stent 100 has been contracted. For this reason, after the stent 100 is loaded into the delivery system 20, the part of the delivery system 20 in which the inflow section 110 is accommodated may be bent to a certain angle with respect to the part thereof housing the outflow section 130 and the transition section 120, which enables the delivery system 20 to better conform to the anatomy of blood vessels and to that of the heart in the course of the implantation.

Figure 13:
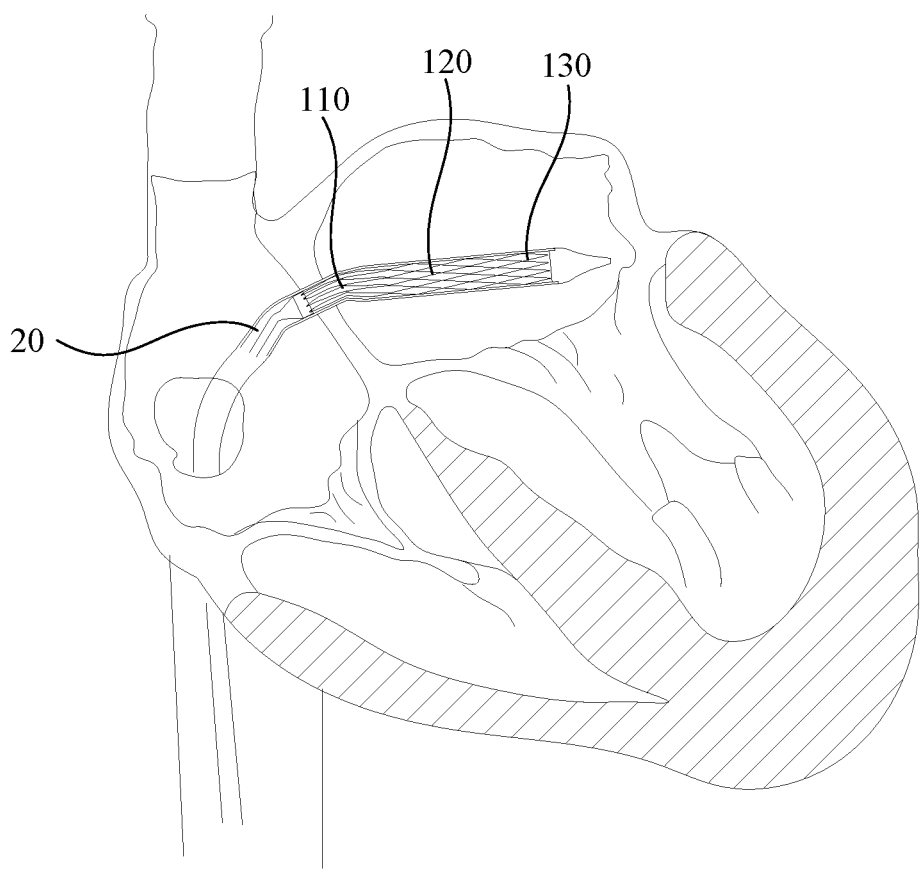

As shown in FIG. 13, in the case of transseptal delivery, after the part of the delivery system 20 housing the outflow section 130 and transition section 120 of the stent 100 has passed through the atrial septum, the part of the delivery system 20 accommodating the inflow section 110 is controlled to be bent to a certain angle with respect to the part housing the outflow section 130 and transition section 120, followed by further advancement of the delivery system 20. During the passage of the delivery system 20 through the atrial septum, the delivery system 20 thus can be operated to avoid causing any damage to the wall of the left atrium or blocking or impeding the advancement of the delivery system 20 due to a relatively great length of the tubular body of the delivery system 20 in which the stent 100 is load and a relatively small size of the left atrium.

During the release, the mesh structure of the inflow section 110, that is braided from filaments, can serve as a buffer for the rapid expansion of the stent 100. The total length of the subvalvular members of the mitral valve prosthesis 10 is configured to be relatively small in order to avoid causing any damage to the subvalvular structure of the native mitral valve. As the diameter of the mitral valve prosthesis 10 is relatively large, the stent 100 will experience significant deformation, which may cause excessive axial displacement of the mitral valve prosthesis 10 relative to the native valve at a later stage of the release. However, according to the present invention, the mesh structure braided from filaments can adapt its shape to changes in the diameter of the stent 100 at the later stage of the release of the mitral valve prosthesis 10 according to the present invention, thereby buffering the radial deformation or axial displacement of the expanding stent 100 and hence allowing enhanced release stability.

Figure 14A:
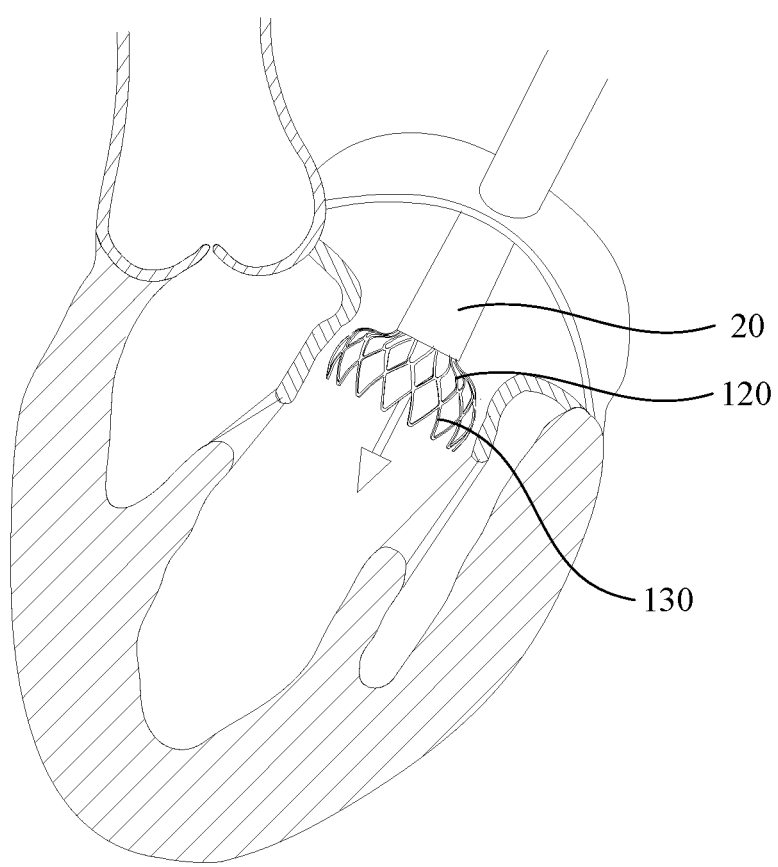
Figure 14B:
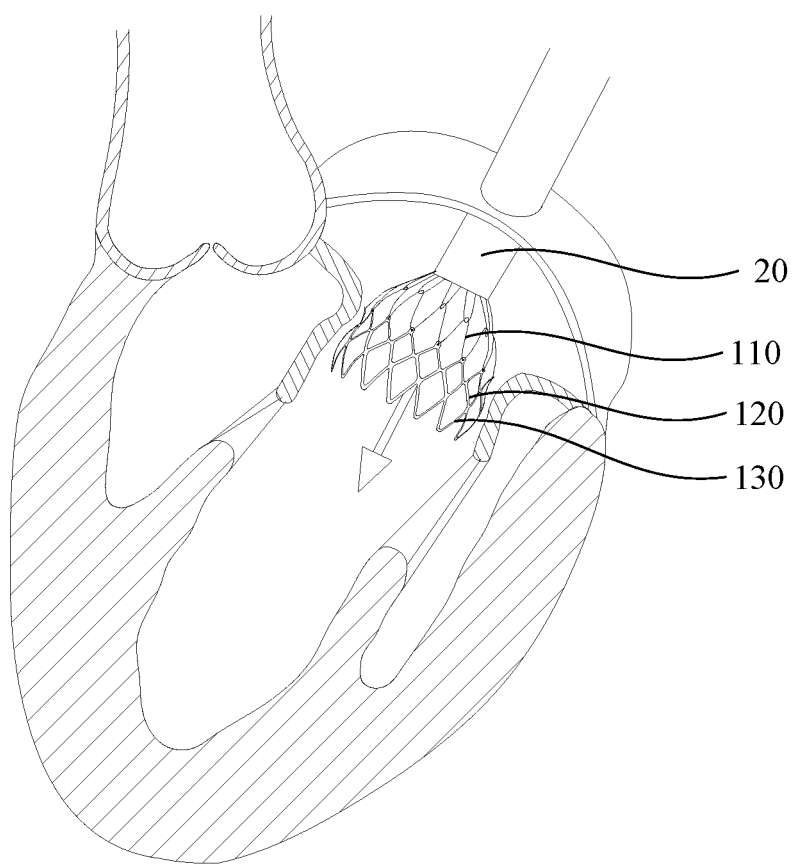
Figure 14C:
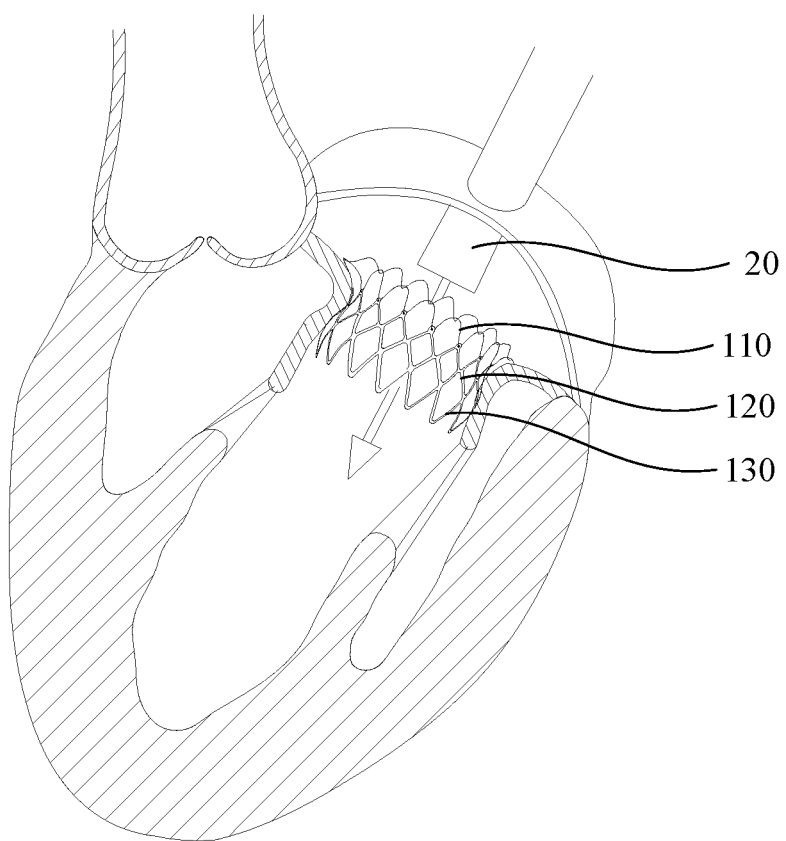

Specifically, reference is now made to FIGS. 14a to 14c, which illustrate the release of a mitral valve prosthesis 10 configured for trans-left atrial or transseptal delivery and implantation. As shown in FIG. 14a, after the outflow section 130 and the transition section 120 are released, the inflow section 110 starts to deform with the continued release of the stent 100. With further expansion of the outflow section 130 and the transition section 120, the inflow section 110 adapts itself to the changing radial dimensions of these subvalvular members. As shown in FIG. 14b, during further release of the inflow section 110, the outflow section 130 and the transition section 120 become fully expanded and the prosthetic leaflet 210 starts to function. Referring to FIG. 14c, following the functioning of the prosthetic leaflet 210, release of the inflow section 110 continues until the prosthetic valve is entirely released.

Figure 15:
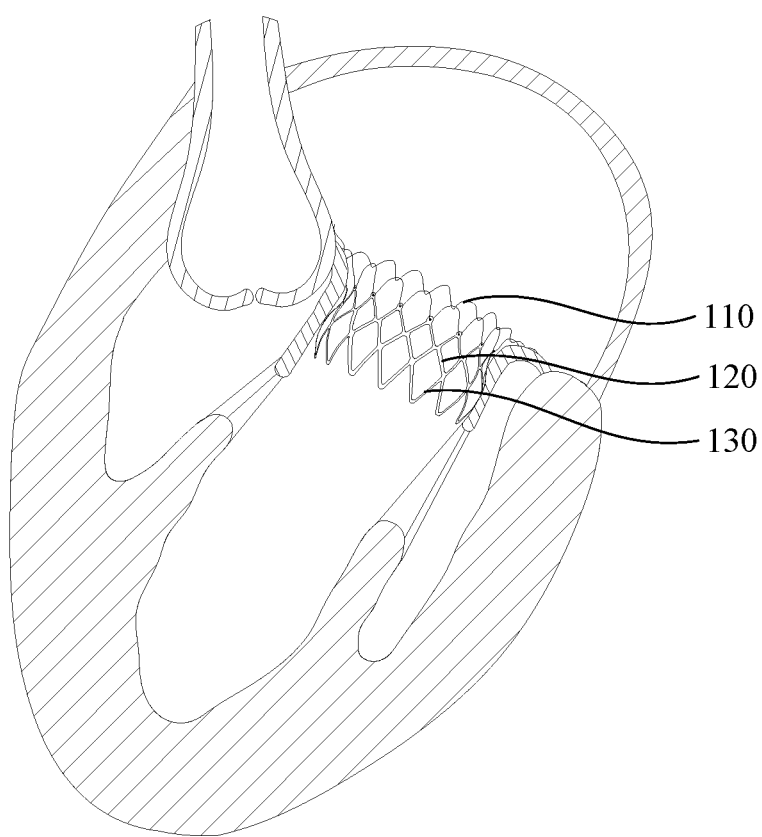

As shown in FIG. 15, after the mitral valve prosthesis 10 is implanted, the inflow section 110 of the stent 100 adheres closely to the atrioventricular orifice between the atrium and the ventricle and covers the native mitral annulus. After the inflow section 110 is released from the delivery system 20, it expands radially with respect to the valve and covers the atrioventricular orifice, with the skirt 220 shielding the left ventricular inflow section to prevent blood from flowing back into the left atrium along the circumference of the stent 100 when the heart contracts. The anterior mitral leaflet is a fibrous extension of the aortic valve and defines the left ventricular inflow section together with the posterior leaflet, as well as the left ventricular outflow section together with the opposing heart septum. Therefore, there is a risk of occlusion of the left ventricular outflow section resulting from an implanted mitral valve prosthesis. However, according to the present invention, the inflow section 110 is low in radial rigidity. For example, when formed by braided filaments, the inflow section 110 is overall soft and can well conform to the saddle-like geometry of the mitral annulus. As a result, its pressure and interference on the aortic valve is reduced, which allows a significant reduction in the risk of occlusion of the left ventricle outflow section while ensuring normal functioning of the inflow section 110.

The tricuspid valve is the right atrioventricular valve, which has a similar structure to the mitral valve and also includes the leaflets, annulus, chordae tendineae, papillary muscles and cardiac muscles. The mitral valve prosthesis 10 configured to replace the native mitral valve may also be used to replace the native tricuspid valve. Specifically, in an embodiment, a tricuspid valve prosthesis is further provided which has the same structure as the mitral valve prosthesis 10 as defined above.

The features of the above-described embodiments may be combined in any suitable manner. While not all possible combinations of these features are described for the sake of brevity, they are all considered within the scope of this specification as long as they there is no contradiction therein.

The foregoing embodiments represent merely a few embodiments of the present invention, and while they have been described above specifically and in detail, they are not intended to be understood as limiting the scope of the present invention. It is noted that, although many variations and modifications can be made by those of ordinary skill in the art without departing from the spirit of the present invention, they all fall into the scope of protection of the present invention as defined by the appended claims.

The invention claimed is:

1. A stent, configured to support a mitral valve prosthesis or a tricuspid valve prosthesis, the stent having a contracted configuration for delivery and an expanded configuration for deployment, wherein the stent comprises, along an axial direction thereof, an inflow section, a transition section, an outflow section, the transition section having two ends respectively connected to the inflow section and to the outflow section; the inflow section is located, when in the expanded configuration, upstream of the outflow section with respect to a blood flow direction; the inflow section extends along the axial direction of the stent away from the transition section and flares out; the inflow section has a mesh structure formed by braided filaments; the transition section and the outflow section have mesh structures formed by cutting tubes; the mesh structure of the inflow section is configured to cover an atrioventricular orifice and optionally further extend from an annulus over at least part of an atrium when the stent has been deployed and is in the expanded configuration;

wherein the mesh structure of the inflow section comprises a plurality of first mesh cells;

wherein in the expanded configuration, those of the first mesh cells corresponding to an anterior portion of a native annulus are axially longer than those of the first mesh cells corresponding to a posterior portion of the native annulus.

2. The stent according to claim 1, wherein
the plurality of first mesh cells are arranged in a plurality of rows each of which contains equally sized ones of the plurality of first mesh cells, and sizes of the plurality of first mesh cells arranged in the plurality of rows increase row by row from one of the rows proximal to the transition section to one of the rows distal from the transition section.

3. The stent according to claim 1, wherein the plurality of first mesh cells are arranged in one row.

4. The stent according to claim 1, wherein at least part of the filaments forming the mesh structure of the inflow section are connected to the transition section by braiding.

5. The stent according to claim 4, wherein
the transition section comprises a plurality of second mesh cells which are arranged in one or more rows;

at least some of the second mesh cells at an end of the transition section proximal to the inflow section are provided with connecting holes, and the filaments of the inflow section pass through at least some of the connecting holes before forming those of the first mesh cells adjacent to the transition section, or the filaments of the inflow section wound around at least some of the second mesh cells at an end of the transition section proximal to the inflow section before forming those of the first mesh cells adjacent to the transition section, or at least some of the second mesh cells at an end of the transition section proximal to the inflow section are provided with connecting rods projecting away from the inflow section, and the filaments of the inflow section are wounded over the connecting rods or around those of the second mesh cells near the connecting rods.

6. The stent according to claim 4, wherein
the transition section comprises a plurality of second mesh cells which are arranged in one or more rows;

connecting holes are provided near apices of at least some of the second mesh cells located at an end of the transition section proximal to the inflow section, and the filaments of the inflow section pass through at least some of the connecting holes before forming those of the first mesh cells adjacent to the transition section, or the filaments of the inflow section wound for at least one turn around apices of at least some of the second mesh cells located at an end of the transition section proximal to the inflow section before forming those of the first mesh cells adjacent to the transition section, or connecting rods projecting away from the inflow section are provided near apices of at least some of the second mesh cells located at an end of the transition section proximal to the inflow section, and the filaments of the inflow section are wounded over the connecting rods or around those of the second mesh cells near the connecting rods.

7. The stent according to claim 1, wherein the mesh structure of the transition section comprises a plurality of second mesh cells, and
wherein at least one annular connecting member is formed around an apex of each of at least some of the first mesh cells of the inflow section proximal to the transition section, at least one connecting hole is provided on at least some of the second mesh cells of the transition section proximal to the inflow section, and the transition section and the inflow section are fixedly connected by inserting a rivet through each of the at least one annular connecting member and a corresponding one of the at least one connecting hole.

8. The stent according to claim 1, wherein the mesh structure of the transition section comprises a plurality of second mesh cells, and
wherein at least one annular connecting member is formed around an apex of each of at least some of the first mesh cells of the inflow section proximal to the transition section, at least one threaded hole is provided on at least some of the second mesh cells of the transition section proximal to the inflow section, and the transition section and the inflow section are fixedly connected by inserting a screw through each of the at least one annular connecting member and a corresponding one of the at least one threaded hole to form a threaded connection between the screw and a corresponding one of the second mesh cells.

9. The stent according to claim 1, further comprising a connecting feature having one end secured to the inflow section and another end secured to the transition section and/or the outflow section.

10. The stent according to claim 9, wherein the mesh structure of the transition section comprises a plurality of second mesh cells, and
wherein at least one annular connecting member is formed around an apex of each of at least some of the first mesh cells of the inflow section proximal to the transition section, at least one connecting hole is provided on at least some of the second mesh cells of the transition section proximal to the inflow section, and
the stent comprises at least two connecting features each having two ends respectively connected to one of the annular connecting features and to one of the connecting holes.

11. The stent according to claim 9, wherein the mesh structure of the transition section comprises a plurality of second mesh cells, and wherein the connecting feature is a sheet-like member which is made of a macromolecular material and has two ends one secured to the inflow section and the other to the transition section and/or the outflow section.

12. The stent according to claim 1, wherein the mesh structure of the outflow section comprises a plurality of third mesh cells which are arranged in one or more rows and are arranged in connection with or separated from each other.

13. The stent according to claim 1, wherein the mesh structures of the outflow section and the transition section are integrally fabricated by cutting a single tube.

14. A mitral valve prosthesis, comprising
a valve assembly; and
a stent, configured to support a mitral valve prosthesis or a tricuspid valve prosthesis, the stent having a contracted configuration for delivery and an expanded configuration for deployment, wherein the stent comprises, along an axial direction thereof, an inflow section, a transition section, an outflow section, the transition section having two ends respectively connected to the inflow section and to the outflow section; the inflow section is located, when in the expanded configuration, upstream of the outflow section with respect to a blood flow direction; the inflow section extends along the axial direction of the stent away from the transition section and flares out; the inflow section has a mesh structure formed by braided filaments; the transition section and the outflow section have mesh structures formed by cutting tubes; the mesh structure of the inflow section is configured to cover an atrio-ventricular orifice and optionally further extend from an annulus over at least part of an atrium when the stent has been deployed and is in the expanded configuration;
wherein the valve assembly is attached to the stent;
wherein the mesh structure of the inflow section comprises a plurality of first mesh cells;
wherein in the expanded configuration, those of the first mesh cells corresponding to an anterior portion of a native annulus are axially longer than those of the first mesh cells corresponding to a posterior portion of the native annulus.

15. The mitral valve prosthesis according to claim 14, wherein the valve assembly comprises a prosthetic leaflet and a skirt in connection with the prosthetic leaflet; the prosthetic leaflet is secured to both of the transition section and the outflow section; the skirt is secured to both of the inflow section and the transition section, or to each of the inflow section, the transition section and the outflow section.

16. A tricuspid valve prosthesis, comprising
a valve assembly; and
a stent, configured to support a mitral valve prosthesis or a tricuspid valve prosthesis, the stent having a contracted configuration for delivery and an expanded configuration for deployment, wherein the stent comprises, along an axial direction thereof, an inflow section, a transition section, an outflow section, the transition section having two ends respectively connected to the inflow section and to the outflow section; the inflow section is located, when in the expanded configuration, upstream of the outflow section with respect to a blood flow direction; the inflow section extends along the axial direction of the stent away from the transition section and flares out; the inflow section has a mesh structure formed by braided filaments; the transition section and the outflow section have mesh structures formed by cutting tubes; the mesh structure of the inflow section is configured to cover an atrio-ventricular orifice and optionally further extend from an annulus over at least part of an atrium when the stent has been deployed and is in the expanded configuration;
wherein the valve assembly is attached to the stent;
wherein the mesh structure of the inflow section comprises a plurality of first mesh cells;
wherein in the expanded configuration, those of the first mesh cells corresponding to an anterior portion of a native annulus are axially longer than those of the first mesh cells corresponding to a posterior portion of the native annulus.

17. The tricuspid valve prosthesis according to claim 16, wherein the valve assembly comprises a prosthetic leaflet and a skirt in connection with the prosthetic leaflet; the prosthetic leaflet is secured to both of the transition section and the outflow section; the skirt is secured to both of the inflow section and the transition section, or to each of the inflow section, the transition section and the outflow section.

* * * * *